US009205212B2

(12) United States Patent
Resca et al.

(10) Patent No.: US 9,205,212 B2
(45) Date of Patent: Dec. 8, 2015

(54) TRANSTRACHEAL CATHETER APPARATUS

(75) Inventors: Daniele Resca, San Felice Sul Panaro (IT); Giuseppe Zucchi, San Possidonio (IT); Alessandra Pedarzini, Finale Emilia (IT); Wilbert Arthur Bosman, La Zwolle (NL)

(73) Assignee: Covidien AG, Neuhausen am Rheinfall (CH)

( * ) Notice: Subject to any disclaimer, the term of this patent is extended or adjusted under 35 U.S.C. 154(b) by 305 days.

(21) Appl. No.: 13/496,710

(22) PCT Filed: Jul. 27, 2010

(86) PCT No.: PCT/EP2010/060870
§ 371 (c)(1),
(2), (4) Date: Apr. 10, 2012

(87) PCT Pub. No.: WO2011/038951
PCT Pub. Date: Apr. 7, 2011

(65) Prior Publication Data
US 2012/0204883 A1    Aug. 16, 2012

(30) Foreign Application Priority Data
Oct. 1, 2009  (EP) ..................................... 09171965

(51) Int. Cl.
*A61M 16/00*  (2006.01)
*A62B 9/06*  (2006.01)
*A61M 16/04*  (2006.01)

(52) U.S. Cl.
CPC ......... *A61M 16/0465* (2013.01); *A61M 16/047* (2013.01); *A61M 16/0418* (2014.02); *A61M 16/0488* (2013.01)

(58) Field of Classification Search
USPC .......................... 128/200.26, 207.14–207.15
See application file for complete search history.

(56) References Cited

U.S. PATENT DOCUMENTS

| | | | | | |
|---|---|---|---|---|---|
| 4,033,353 | A | * | 7/1977 | La Rosa | 128/207.15 |
| 4,067,331 | A | * | 1/1978 | Berman | 128/200.26 |
| 4,512,765 | A | * | 4/1985 | Muto | 604/119 |
| 4,685,457 | A | | 8/1987 | Donenfeld | |
| 5,031,613 | A | * | 7/1991 | Smith et al. | 128/207.14 |
| 5,181,509 | A | * | 1/1993 | Spofford et al. | 128/207.14 |
| 5,655,518 | A | * | 8/1997 | Burden | 128/200.26 |
| 6,655,382 | B1 | * | 12/2003 | Kolobow | 128/204.25 |
| 7,588,033 | B2 | * | 9/2009 | Wondka | 128/207.14 |
| 2004/0221852 | A1 | * | 11/2004 | Madsen | 128/207.14 |
| 2004/0221853 | A1 | * | 11/2004 | Miller | 128/207.14 |
| 2007/0181130 | A1 | | 8/2007 | Worley | |
| 2008/0216839 | A1 | | 9/2008 | Rutter | |
| 2009/0064999 | A1 | * | 3/2009 | Marten et al. | 128/200.26 |

FOREIGN PATENT DOCUMENTS

WO    86/03127  A1    6/1986

OTHER PUBLICATIONS

International Search Report for Appln. No. PCT/EP2010/060870 mailed Nov. 8, 2010.

* cited by examiner

*Primary Examiner* — Kristen Matter
(74) *Attorney, Agent, or Firm* — Carter, DeLuca, Farrell & Schmidt, LLP

(57) ABSTRACT

A catheter apparatus (10) for transtracheal administration of supplemental oxygen to a patient in need of continuous long term oxygen therapy.

13 Claims, 2 Drawing Sheets

TRANSTRACHEAL CATHETER APPARATUS

CROSS-REFERENCE TO RELATED APPLICATIONS

This application is a U.S. National Stage Application filed under 35 U.S.C. §371(a) of International Application No. PCT/EP2010/060870, filed Jul. 27, 2010, which claims the benefit of and priority to EP Patent Application No. 09171965.8, filed Oct. 1, 2009, the entire contents of which are incorporated by reference herein.

TECHNICAL FIELD

The invention concerns a transtracheal catheter apparatus.

In particular, the invention relates to a transtracheal catheter apparatus for transtracheal administration of supplemental oxygen to a patient in need of continuous long term oxygen therapy (usually COPD-Chronic Obstructive Pulmonary Disease—Patients).

BACKGROUND ART

Since the early seventies various devices and methods have been devised for providing a tracheostomy tube so that a patient whose airway is otherwise blocked may continue to breathe. Such devices, were generally intended only for use with a patient who is not breathing spontaneously and are not intended for the long-term oxygen supplementation therapy for chronic lung disease. The use of such tubes had been restricted medically to emergency situations where the patient would otherwise suffocate due to the blockage of the airway. Such emergency tracheotomy tubes were not intended for long-term oxygen supplementation therapy after the airway blockage is removed.

On the basis of this known practice, EP 207 099 discloses a transtracheal system and method for supplying of supplemental oxygen to patient through a transtracheal catheter instead of commonly used devices such as nasal cannulas.

This procedure even if performable only on a selected number of patients, allows better psychological acceptance of the treatment, better quality of life and reduced consumption of oxygen.

Nevertheless, known systems for transtracheal administration of supplemental oxygen through a transtracheal catheter have some drawbacks.

For example, some of these drawbacks are related to:
frequent dislodgements of the catheter;
risk of kinking of the catheter near the stoma;
risk that the catheter tip comes into contact with the posterior wall of the trachea, causing it injuries;
leakage of oxygen from the stoma to the environment.

It is an object of the present invention to overcome the drawbacks above.

DISCLOSURE OF THE INVENTION

This object is achieved by a transtracheal catheter for transtracheal administration of supplemental oxygen according to any of the claims below.

BRIEF DESCRIPTION OF THE DRAWINGS

The transtracheal catheter is shown in the following drawings, given purely by way of a non-limiting examples, in which.

DETAILED DESCRIPTION OF THE PREFERRED EMBODIMENTS OF THE INVENTION

The transtracheal catheter apparatus 10 is part of a system of transtracheal administration of oxygen described in its entirety in a different patent application filed in the name of the same Applicant.

The transtracheal catheter apparatus 10 comprises a catheter tube 1.

According to the drawings, the transtracheal catheter tube 1 is designed in a way as to match in size with a cannula 2 positioned inside a stoma previously formed on the trachea by means of a surgical or percutaneous technique.

Figure 1:
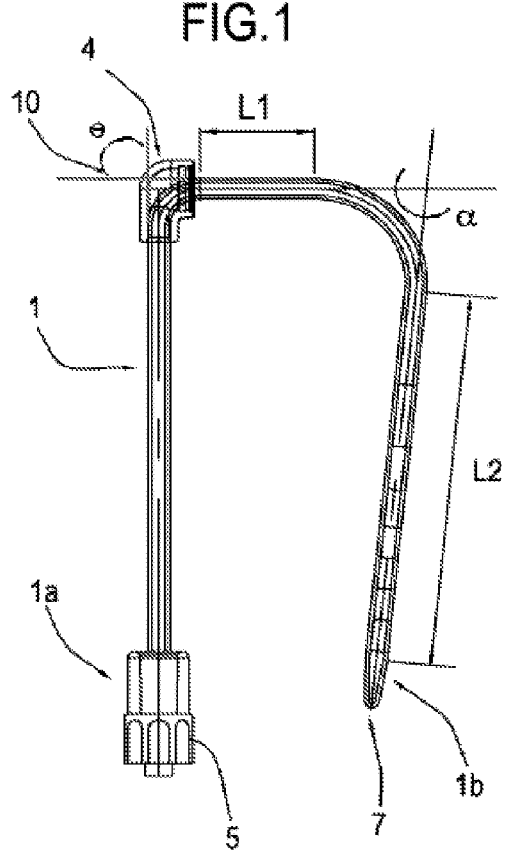
FIG. 1 shows, in schematic lateral view with some sectioned parts, the catheter apparatus of the present invention.
Figure 2:
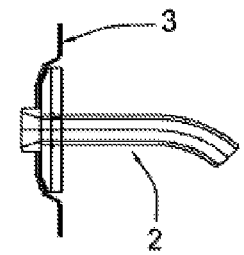
FIGS. 2 to 4 show respectively schematic views of different elements of the catheter apparatus of the present invention and of the system for applying it.
Figure 5:
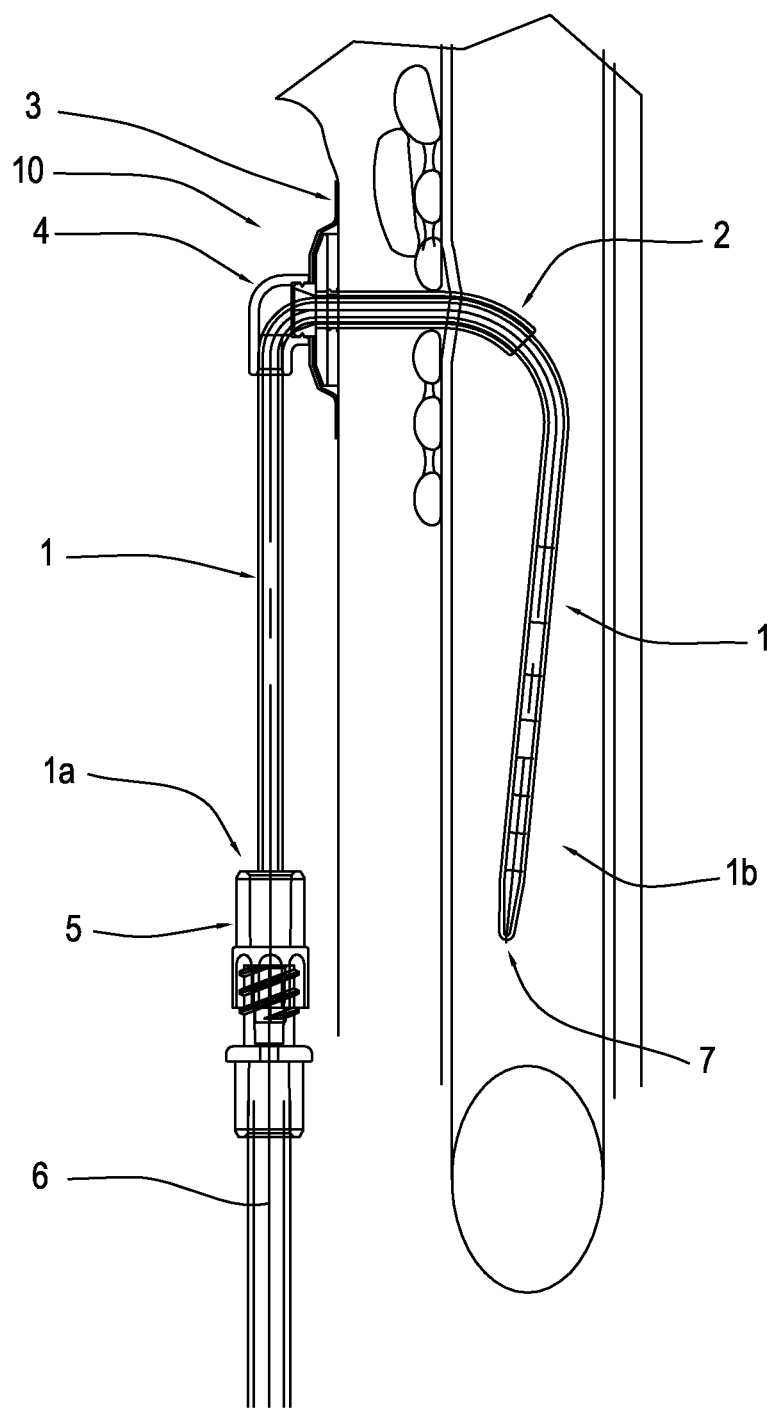
FIG. 5 shows, in a schematic view with some sectioned parts, the catheter apparatus of the present invention in use, applied in a human trachea, by way of example.

Once the cannula 2 is fixed to the patient skin by an adhesive patch 3 (FIGS. 1 and 5), the transtracheal catheter tube 1 can be inserted inside the cannula 2 itself.

The transtracheal catheter tube 1 (hereafter referred to as catheter tube 1) is made of flexible material, resistant enough to kinking. The flexible material is preferably transparent.

The catheter tube 1 advantageously presents a longitudinal radiopaque line (not illustrated) to allow verification of correct positioning through x-rays.

The catheter tube 1 is pre-formed with a reversed U shape.

The catheter tube 1 comprises two portions L1 and L2 of variable length.

Advantageously, instead of a regular reversed U shape it is beneficial to have the second angle α of the transtracheal catheter (i.e. the angle between the extensions of portion L1 and portion L2 in the trachea) less than 90°-around 80° for instance—to ascertain that the tracheal portion can preferably position near the front wall of the trachea instead of the back wall.

The first portion L1 is equivalent to the length L of the cannula 2. The second portion L2 represents at least approximately the length of the tracheal portion of the catheter and can vary in relation to the physiology of the patient (different catheters having different lengths L1 and L2 will be provided).

Advantageously, thanks to the pre-shaping of the transtracheal catheter tube 1 the patient and/or his caregiver do not have to worry about its positioning, which is otherwise bound by the mutual shape equivalence in the contact areas with the cannula 2.

Optimal fixing of transtracheal catheter tube 1 is further ensured by an elbow connector 4, sliding on the external surface of the catheter tube 1 itself.

The elbow connector 4 is preferably made from a soft rubber and defines a first angle θ.

Figure 3:
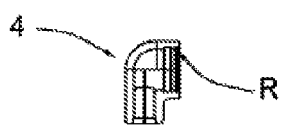
Figure 4:
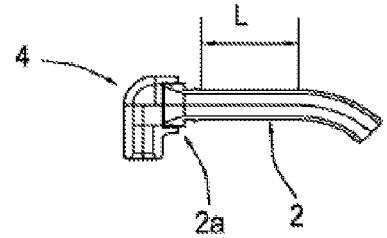

The elbow connector 4 is to be secured on a proximal end 2a of the cannula 2 by means of an inner gripping ring R (see FIGS. 3 and 4).

According to an equivalent embodiment not illustrated, the cannula 2 presents an annular recess able to match with said gripping ring R or equivalent gripping means arranged on the elbow connector 4.

The elbow connector 4 ensures at the same time sealing between the transtracheal catheter tube 1 and the cannula 2 itself, preventing any fluid leakage from the trachea to the outside.

The catheter tube 1 presents a proximal end 1a and an opposite distal end 1b, located in the tracheal portion of the catheter tube 1 itself.

The catheter apparatus 10 comprises, by the proximal end 1a of the catheter tube 1, connection means 5 for fitting with a oxygen supply tubing 6.

The tracheal portion of the catheter tube 1, by its distal end 1b, has a spherical/ball tip 7 to enhance atraumaticity during insertion and once in place during patient movements.

Advantageously, the spherical/ball tip 7 is closed.

The tracheal portion of the transtracheal catheter tube 1 presents a plurality of holes (not illustrated) for the oxygen diffusion. Said holes are advantageously distributed along a spiral line around the tracheal portion of the transtracheal catheter 1.

The transtracheal catheter apparatus 10 according to the present invention provides a plurality of advantages with respect to the prior art.

Some of the advantages that the transtracheal catheter apparatus 10 is able to contribute are described below.

In particular, the use of the transtracheal catheter apparatus 10 according to the present invention allows:

- to reduce the risk that the transtracheal catheter tip comes into contact with the back wall of the trachea, due to the particular reversed U shape of the catheter tube 1; as above described the non regular reversed U shape having the second angle α of the catheter tube lower than 90°, permits to ascertain that the tracheal catheter portion can preferably be positioned near the front wall of the trachea instead of the back wall, which is the most sensible and less protected part of the trachea, thus increasing the safety of the patient;
- the homogeneous diffusion of oxygen thanks to the presence of a plurality of holes, advantageously spirally distributed around the tracheal catheter portion; said homogeneous diffusion leads to a minimization of irritations due to the impact velocity of oxygen toward the mucosa in contrast to the traditional system where there is only one lumen oriented towards the carena, this advantage increasing the safety of the patient;
- to minimize the risk of injury of the back wall during catheter insertion and also of any additional accidental contact with the tracheal walls during use, due to the spherical/ball shape of the tip 7, thus increasing the safety of the patient;
- to eliminate snake movement of the known catheters during high flow oxygen administration thanks to the closed catheter tip, thus increasing the safety of the patient;
- insertion of the transtracheal catheter tube without the need of a mandrel which was present in systems according to the state of the art; thus increasing safety and usability;
- better sealing between the stoma and the transtracheal catheter thanks to the use of the elbow connector 4 matching with the cannula 2, thus achieving no leakage of oxygen from the stoma to the environment and less contact between the trachea and the external environment, in this way increasing the safety of the patient with a reduced risk of cross contamination;
- less misplacement of the transtracheal catheter during use, now occurring with state of the art catheters, increasing safety and usability.

In fact, it is known that most of the complications associated with the use of the traditional transtracheal system occurs during the latter phase once the stent is exchanged for the functioning catheter (SCOOP). Since the insertion tract is not yet mature the catheter may easily become dislodged and accidental displacement of the catheter usually occurs at night with severe consequences for the patient such as respiratory distress, hypoxemia and subcutaneous emphysema.

The invention claimed is:

1. A catheter apparatus for transtracheal administration of oxygen comprising a catheter tube having a first portion and a second portion, the first portion being passed through an elbow connector so as to have a 90° bend defining a first angle θ at an intermediate position between a proximal end and a distal end of the first portion, the distal end of the first portion and the second portion defining a second angle α, the second angle α being lower than 90° and pre-formed into the catheter tube such that the second portion is configured to bias towards an anterior side of a patient's trachea, wherein the first angle θ and second angle α define a reversed U-shape.

2. A catheter apparatus as claimed in claim 1, wherein the catheter tube comprises a ball tip which defines a distal end of the second portion.

3. A catheter apparatus as claimed in claim 2, wherein the ball tip is closed.

4. A catheter apparatus as claimed in claim 1, wherein the elbow connector is securable to a cannula inserted in a stoma.

5. A catheter apparatus as claimed in claim 4, wherein the elbow connector includes a gripping means to stably connect to the cannula.

6. A catheter apparatus as claimed in claim 5, wherein the cannula has an annular recess abutting the gripping means of the elbow connector.

7. A catheter apparatus as claimed in claim 1, wherein the second portion includes a plurality of holes for oxygen diffusion.

8. A catheter apparatus as claimed in claim 7, wherein the plurality of holes are distributed along a spiral line.

9. A catheter apparatus as claimed in claim 1, wherein the second angle α is about 80°.

10. A catheter apparatus as claimed in claim 1, wherein the elbow connector is slidable along the first portion.

11. A catheter apparatus as claimed in claim 10, wherein sliding the elbow connector varies a length of the first portion with respect to a length of the second portion.

12. A catheter apparatus as claimed in claim 1, wherein the first portion is bent inside the elbow connector.

13. A catheter apparatus as claimed in claim 1, further including a longitudinal radiopaque line disposed on the catheter tube.

* * * * *